(12) United States Patent
Laine

(10) Patent No.: US 11,951,268 B2
(45) Date of Patent: Apr. 9, 2024

(54) WIRE HOLDER FOR STERILE FIELD

(71) Applicant: Andrea Laine, Wailuku, HI (US)

(72) Inventor: Andrea Laine, Wailuku, HI (US)

( * ) Notice: Subject to any disclaimer, the term of this patent is extended or adjusted under 35 U.S.C. 154(b) by 403 days.

(21) Appl. No.: 17/403,965

(22) Filed: Aug. 17, 2021

(65) Prior Publication Data

US 2023/0059137 A1    Feb. 23, 2023

(51) Int. Cl.
*A61M 25/09* (2006.01)

(52) U.S. Cl.
CPC ....... *A61M 25/09* (2013.01); *A61M 2209/084* (2013.01)

(58) Field of Classification Search
CPC ............ A61M 25/09; A61M 2209/084; A61M 25/002; A61B 50/20
See application file for complete search history.

(56) References Cited

U.S. PATENT DOCUMENTS

| 2007/0084625 A1* | 4/2007 | Martin | H02G 3/04 174/135 |
| 2011/0147542 A1* | 6/2011 | Hoek | H02G 3/32 248/68.1 |

* cited by examiner

*Primary Examiner* — Daniel McNally
(74) *Attorney, Agent, or Firm* — Larson & Larson; Frank Liebenow; Justin P. Miller

(57) ABSTRACT

A wire manager for managing wires in a sterile field includes a base that is planar and has a width, a depth, and a height and has a sticky material disposed on a first side for temporarily adhering the base to a surface of the sterile field. There are capture loops stacked and depending from an edge of a second side of the base and separators that are planar, an edge of each separator is connected to one of the capture loops. Each of the separators is flexible and resilient. In some embodiments, each of the separators has a separator width that is equal to the width of the base, and each of the separators has a separator depth that is less than the depth of the base.

20 Claims, 4 Drawing Sheets

WIRE HOLDER FOR STERILE FIELD

FIELD

This invention relates to the field of interventional radiology and cardiac catheterization lab and more particularly to a system for managing wires at a sterile field.

BACKGROUND

When performing various types of procedures, for example, in an interventional radiology room, there are often many catheters or wires used. Some catheters or wires, for example, are for performing the actual procedure, including catheters, guide wires, glide wires, etc.

What is needed is a system that will manage and organize wires in a sterile environment such as a procedural room.

SUMMARY

In one embodiment, an apparatus for managing wires in a sterile field is disclosed including a base that has a sticky material disposed on a first side for temporarily adhering the base to a surface of the sterile field. The apparatus for managing wires has capture loops stacked and depending from an edge of a second side of the base and there are separators, an edge of each is connected to one of the capture loops. Each of the plurality of separators is flexible and resilient.

In another embodiment, a method of managing wires in a sterile field includes providing the wire manager as described above and affixing the base to a surface within the sterile field by way of the sticky material. At least one of the separators is bent (e.g., by a user's fingers), thereby enlarging a space between that separator and an adjacent separator. A wire is then inserted between that separator and the adjacent separator and then that separator is released thereafter that separator returns to a substantially planar configuration.

In another embodiment, a wire manager for managing wires in a sterile field is disclosed including a base that is planar and has a width, a depth, and a height and has a sticky material disposed on a first side for temporarily adhering the base to a surface of the sterile field. There are capture loops stacked and depending from an edge of a second side of the base and separators that are planar, an edge of each separator is connected to one of the capture loops. Each of the separators is flexible and resilient, each of the separators has a separator width that is equal to the width of the base, and each of the separators has a separator depth that is less than the depth of the base.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
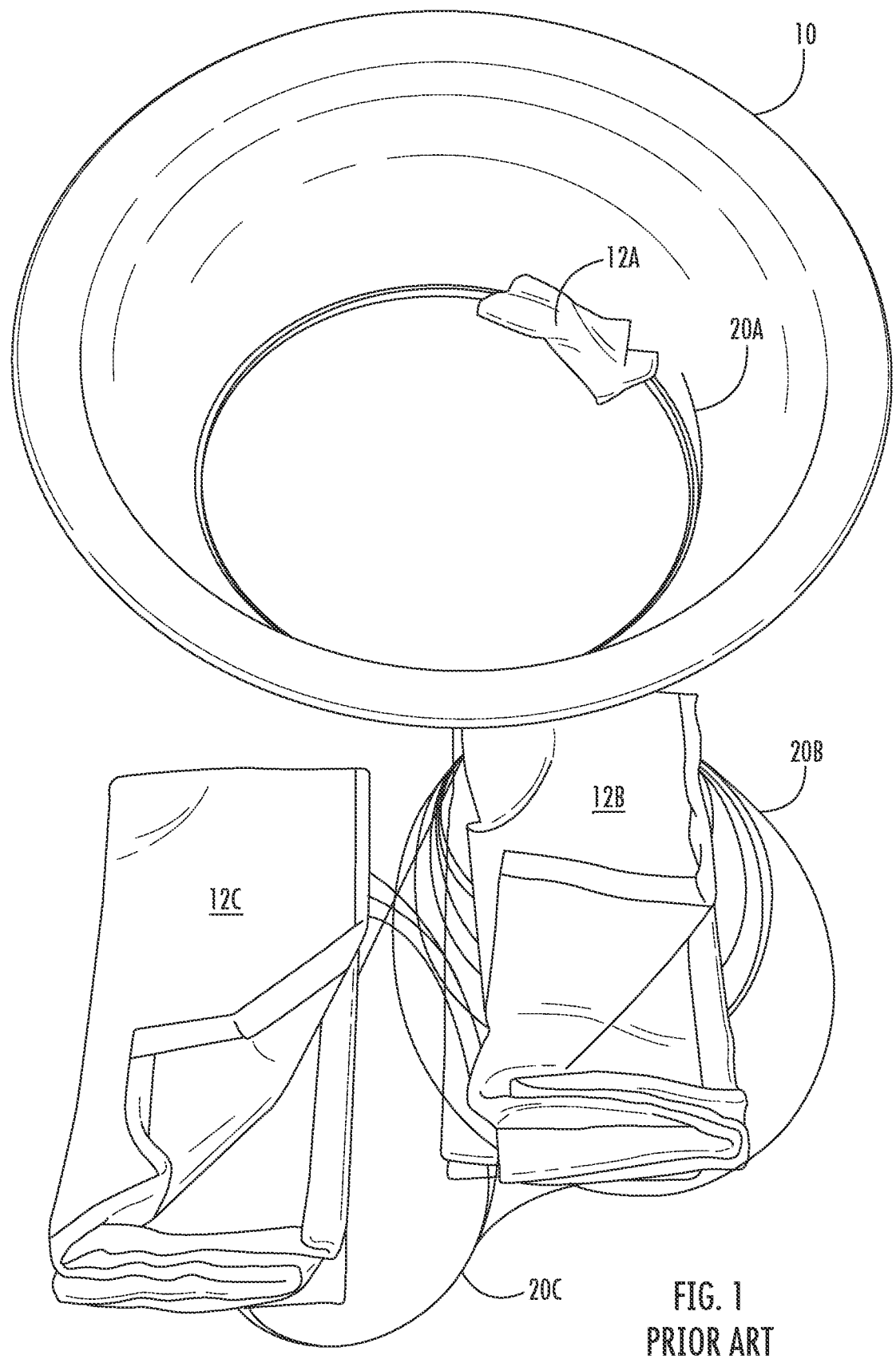
FIG. 1 illustrates a schematic view of a mess of wires in a sterile field such as a procedural table.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a schematic view of a mess of wires of the prior art is shown in a sterile field such as a procedural table. Present day procedural rooms have difficulty managing wires as exemplified in an article titled "Surgery Is An Organized Chaos Of Cords, Tubes And Wires," Sep. 12, 2011, https://getbetterhealth.com/surgery-is-an-organized-chaos-of-cords-tubes-and-wires/. As shown in FIG. 1, there are three wires 20A/20B/20C. An attempt to keep the wires 20A/20B/20C separated is made using silicone pads 12A/12B/12C and a pan 10, but such silicone pads 12A/12B/12C and pan 10 creates other issues in the sterile field such as they occupy critical space, introduce more objects that might create an infection, require disposal after the procedure or sterilization before and after the procedure, etc. As silicone pads 12A/126/12C are often disposed in sterile disposal receptacles after the procedure, the silicone pads 12A/126/12C incur costs to purchase and costs for disposal, not to mention the effect on the environment.

The above notwithstanding, as visible in FIG. 1, the attempts to organize the wires 20A/20B/20C results in chaos in the operating environment a possible tangling which will delay any response to a need for one of the wires 20A/20B/20C for detangling.

Note that throughout this description, the term "wires" refers to any elongated, flexible device such as wires, guide wires, catheters, etc.

Figure 2:
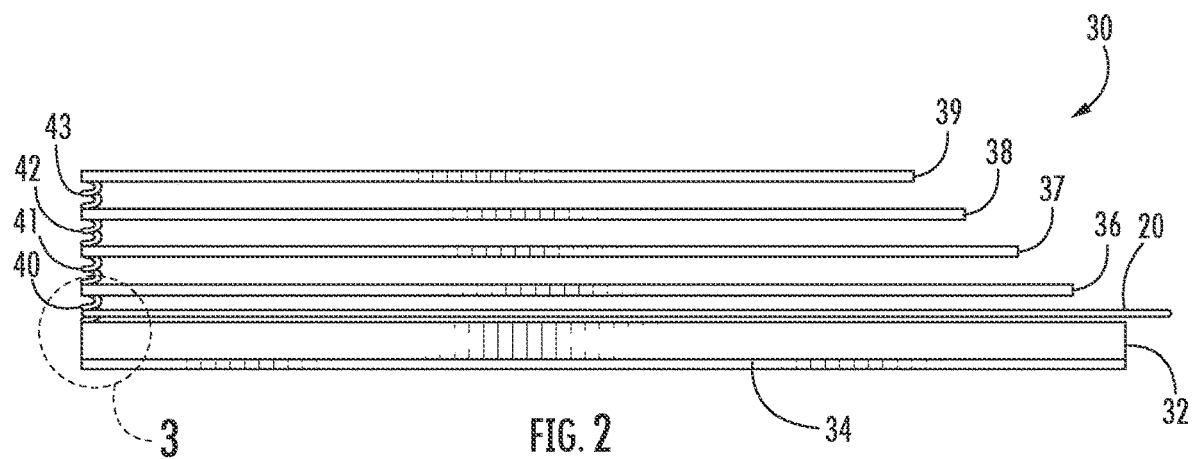
FIG. 2 illustrates an elevational view of the wire holder for a sterile field with a wire.
Figure 3:
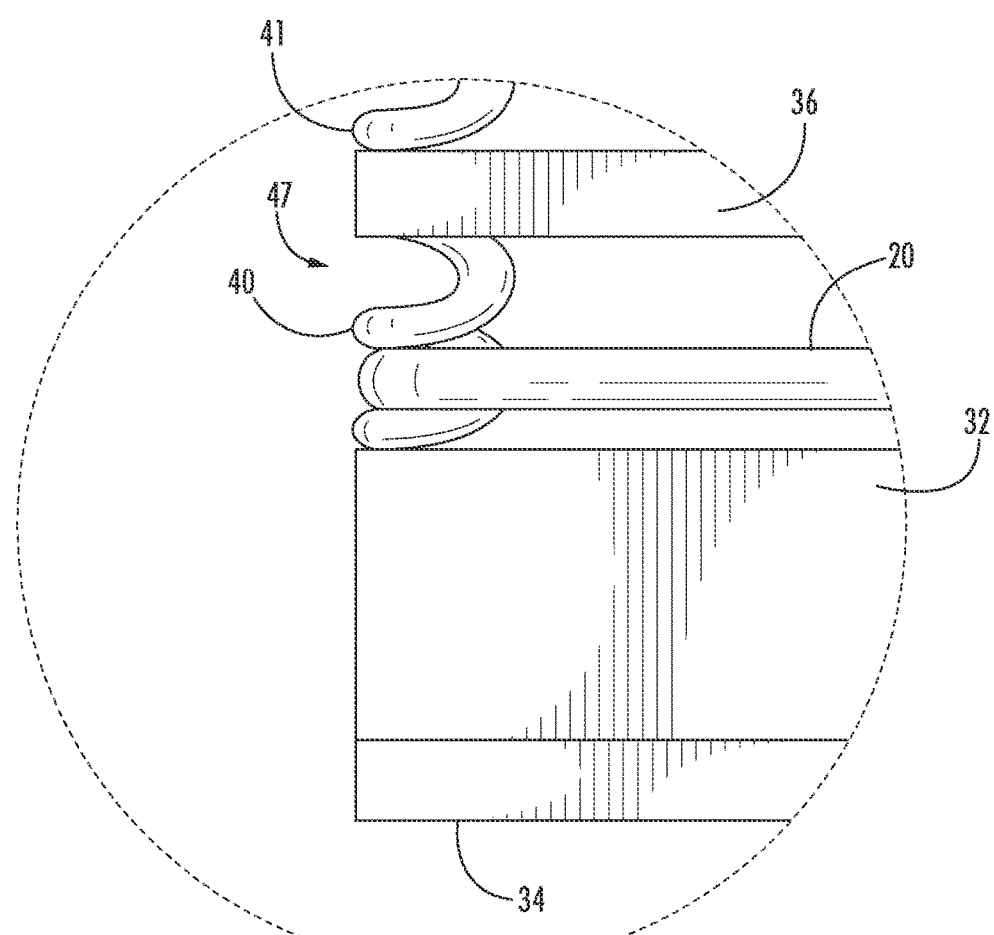
FIG. 3 illustrates an expanded view of the wire holder for the sterile field with the wire.

Referring to FIGS. 2 and 3, views of the wire holder 30 for a sterile field with a wire 20 are shown. The wire holder 30 has a base 32 and several separators 36/37/38/39 between which wires 20 are maintained until needed. In some embodiments, the base 32 is planar and made of a material that is suitable for a sterile field (e.g., a procedure room) and is either stiff or resilient (e.g., slightly bendable but returns to an original shape after the force that caused bending abates). One such material is anticipated to be silicone. In some embodiments, the separators 36/37/38/39 are planar to match the base 32, but each of the separators 36/37/38/39 are not necessarily of the same width and depth as the base 32, allowing for ease of indexing during use.

A bottom surface of the base 32 is coated with an adhesive layer 34 (e.g., an adhesive pad, adhesive pads, continuous sheet of adhesive material, adhesive coating). As the adhesive layer 34 is sticky and is used to hold the wire holder 30 to a surface such as a table on which the procedure is performed or a drape on a sterile field, it is preferred that the adhesive layer 34 be made of a repositionable adhesive (sticky material) or pressure-sensitive adhesive such as Pressure Sensitive Acrylate or microsphere adhesives.

The separators 36/37/38/39 are interfaced at one end by wire capture loops 40/41/42/43 that have one or more indentations 47 for capturing the wires 20 (see FIG. 3 in which the wire 20 passes through the indentations 47). Note that although two of the indentations 47 are shown in the figures, any number of the indentations 47 are anticipated, including one indentation 47. The wire capture loops 40/41/

42/43 connect the separators 36/37/38/39 to each other at an edge of the separators 36/37/38/39 and one wire capture loop 40 connects the bottom separator 36 to the base 32. Note that in some embodiments, the wire capture loops 40/41/42/43 are made from a material such as silicone and bonded or molded to the separators 36/37/38/39 and base 32 while in other embodiments, the wire capture loops 40/41/42/43 are molded together with the separators 36/37/38/39 and base 32, made from the same material, for example, silicone.

In some embodiments, the base 32 is thicker than the separators 36/37/38/39, for example, ¼ of an inch, while in other embodiments, the base 32 and separators 36/37/38/39 are of the same thickness.

In some embodiments, successive separators 36/37/38/39 are shorter than the prior separators 36/37/38/39 as shown in FIG. 2, allowing easier access to each layer of separators 36/37/38/39, while in other embodiments all separators 36/37/38/39 are of the same dimension.

It is preferred that the separators 36/37/38/39 be made of a thickness that provides for flexibility and resilience so that each separator 36/37/38/39 will bend upwards (in a direction away from the base 32) for insertion/removal of the wires 20 under force (e.g., force of a user's fingers) then, upon abatement of such force, the separator 36/37/38/39 restores to a flat configuration by way of resiliency, assuming that no object such as the wire 20 impedes restoration to the planar configuration.

Figure 4:
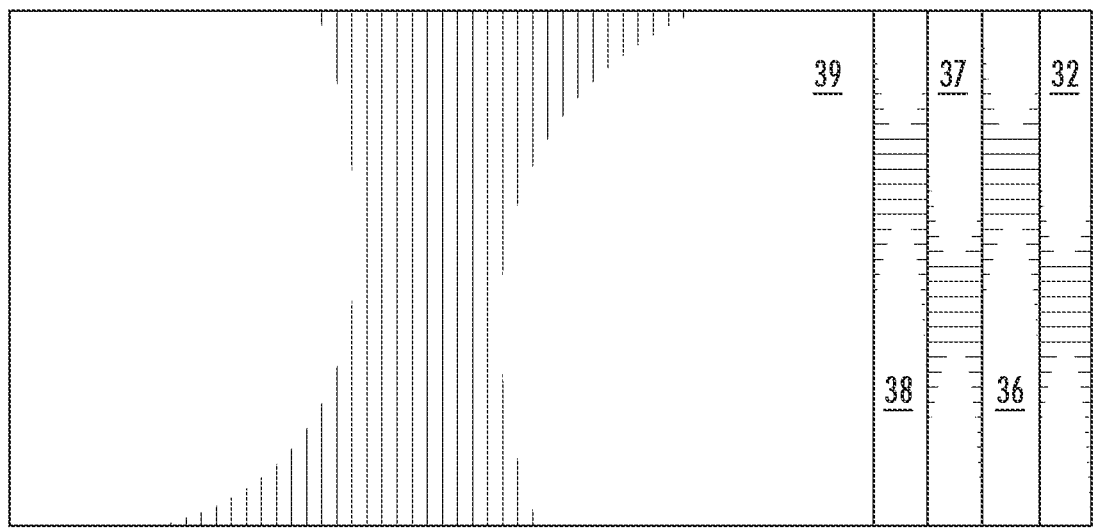
FIG. 4 illustrates a top-plan view of the wire holder for a sterile field.
Figure 6:
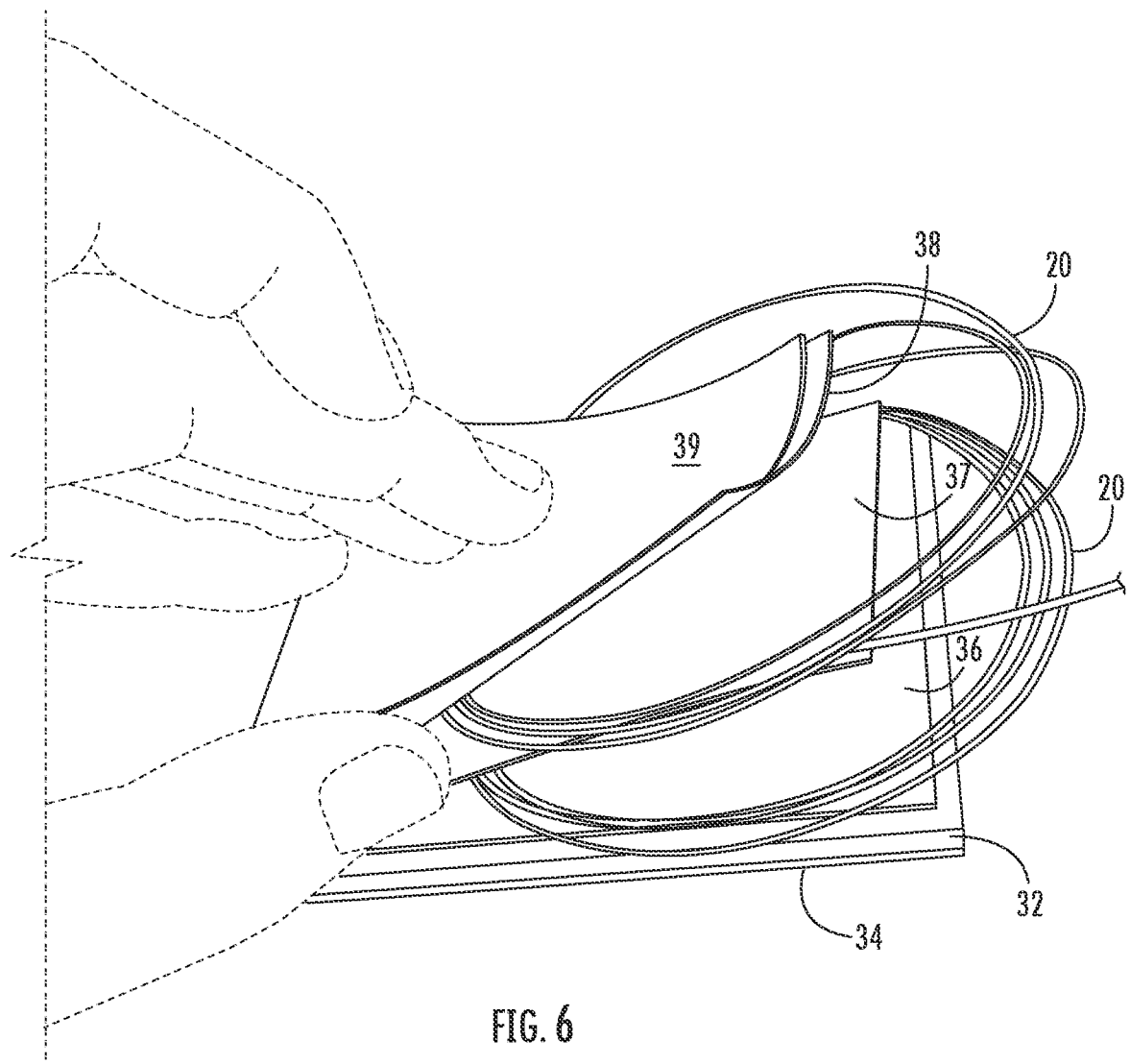
FIG. 6 illustrates a perspective view of the wire holder for a sterile field with wires.

Referring to FIG. 4, a top-plan view of the wire holder 30 for a sterile field is shown. As shown in this embodiment, the separators 36/37/38/39 are planar to match the base 32, and each of the separators 36/37/38/39 are of the same width as the base 32 but vary in depth, allowing for ease of indexing during use as shown in FIG. 6. In this, the top separator 39 (furthest from the base 32) has the shortest depth and the bottom separator 36 has the longest depth, almost as long as the depth of the base 32.

Figure 5:
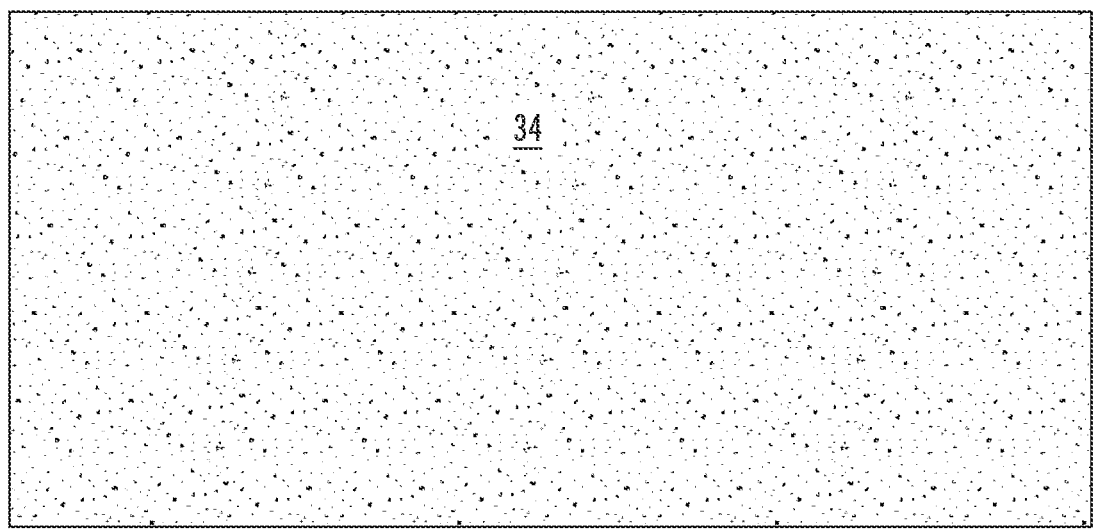
FIG. 5 illustrates a bottom-plan view of the wire holder for a sterile field.

Referring to FIG. 5, a bottom-plan view of the wire holder 30 for a sterile field is shown. In this bottom view, the entire bottom surface of the base 32 is covered with an adhesive layer 34 (e.g., a continuous sheet of adhesive material or an adhesive coating) per one embodiment of the present invention. Note that in other embodiments, an adhesive pad, several adhesive pads, or a section or sections of adhesive coating are on a bottom surface of the base 32. As discussed, the adhesive layer 34 is used to hold the wire holder 30 to a surface such as a table on which a procedure is performed or a drape on a sterile field. Therefore, in one embodiment, the adhesive layer 34 is made of a repositionable adhesive or pressure-sensitive adhesive such as Pressure Sensitive Acrylate or microsphere adhesives. In other embodiments, the adhesive layer 34 is made of any self-sticking material such as double-sided tape. It is fully anticipated that during shipping and storage, a removable cover be placed over the adhesive layer 34 to prevent accumulation of debris and maintain stickiness.

Referring to FIG. 6, a perspective view of the wire holder 30 for a sterile field with wires 20 is shown. In this view, it is shown how several wires 20 are placed between the separators 36/37/38/39. Note how well organized are the wires 20. In this embodiment, successive separators 36/37/38/39 are shorter than the prior separators 36/37/38/39, allowing easier access to each layer of separators 36/37/38/39. Also, in this embodiment, the separators 36/37/38/39 are made of a thickness that provides for flexibility and resilience so that each separator 36/37/38/39 will bend upwards (in a direction away from the base 32) for insertion/removal of the wires 20 under force (e.g., force of a user's fingers) then, upon abatement of such force, the separator 36/37/38/39 restores to a flat configuration by way of resiliency, assuming that no object such as the wire 20 impedes restoration to the planar configuration.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An apparatus for managing wires in a sterile field, the apparatus comprising:
   a base;
   an adhesive material disposed on a first side of the base for temporarily adhering the base to a surface of the sterile field;
   a plurality of capture loops stacked and depending from an edge of a second side of the base;
   a plurality of separators, an edge of each separator connected to one of the plurality of capture loops; and
   whereas each of the plurality of separators is flexible and resilient.

2. The apparatus for managing wires of claim 1, wherein the base is made of silicone.

3. The apparatus for managing wires of claim 1, wherein the plurality of capture loops and the plurality of separators are made of silicone.

4. The apparatus for managing wires of claim 1, wherein the adhesive material is selected from a group consisting of an adhesive pad, a plurality of adhesive pads, a continuous sheet of adhesive, and an adhesive coating.

5. The apparatus for managing wires of claim 1, wherein the adhesive material is pressure sensitive acrylate.

6. The apparatus for managing wires of claim 1, wherein the base, the plurality of capture loops, and the plurality of separators are molded as one piece.

7. A method of managing wires in a sterile field, the method comprising:
   providing the apparatus for managing wires of claim 1;
   affixing the base to a surface within the sterile field by way of the adhesive material;
   bending at least one of the plurality of separators, thereby enlarging a space between the at least one of the plurality of separators and an adjacent one of the plurality of separators;
   inserting a wire between the at least one of the plurality of separators and the adjacent one of the plurality of separators; and
   releasing the at least one of the plurality of separators, thereafter the at least one of the plurality of separators returning to a substantially planar configuration.

8. The method of claim 7, wherein the base is made of silicone.

9. The method of claim 8, wherein the plurality of capture loops and the plurality of separators are made of silicone.

10. The method of claim 7, further comprising removing the base from the surface within the sterile field.

11. The method of claim 7, wherein the adhesive material is selected from a group consisting of an adhesive pad, a plurality of adhesive pads, a continuous sheet of adhesive, and an adhesive coating.

12. The method of claim 7, wherein the adhesive material is pressure sensitive acrylate.

13. The method of claim 7, wherein the base, the plurality of capture loops, and plurality of separators are molded as one piece.

14. A wire manager for managing wires in a sterile field, the wire manager comprising:
a base that is planar and has a width, a depth, and a height;
a sticky material disposed on a first side of the base for temporarily adhering the base to a surface of the sterile field;
a plurality of capture loops stacked and depending from an edge of a second side of the base;
a plurality of separators, each of the plurality of separators are planar, an edge of each separator is connected to one of the plurality of capture loops;
whereas each of the plurality of separators is flexible and resilient; and
whereas each of the plurality of separators has a separator width that is equal to the width of the base and each of the plurality of separators has a separator depth that is less than the depth of the base.

15. The wire manager of claim 14, wherein the base, the plurality of capture loops and the plurality of separators are made of silicone.

16. The wire manager of claim 14, wherein each successive separator of the plurality of separators has the separator depth that is less than the separator depth of a lower one of the plurality of separators, the lower one of the plurality of separators being closer to the base.

17. The wire manager of claim 14, wherein the sticky material is selected from a group consisting of an adhesive pad, a plurality of adhesive pads, a continuous sheet of an adhesive material, and an adhesive coating.

18. The wire manager of claim 14, wherein the sticky material is pressure sensitive acrylate.

19. The wire manager of claim 14, wherein the base, the plurality of capture loops, and the plurality of separators are molded as one piece.

20. The wire manager of claim 14, wherein the height of the base, is greater than a separator height of each of the plurality of separators.

* * * * *